（12）United States Patent
Banerjee et al.

(10) Patent No.: US 8,623,922 B2
(45) Date of Patent: *Jan. 7, 2014

(54) BRONCHODILATING BETA-AGONIST COMPOSITIONS AND METHODS

(75) Inventors: Partha S. Banerjee, Wynnewood, PA (US); Imtiaz A. Chaudry, American Canyon, CA (US); Stephen Pham, Sacramento, CA (US)

(73) Assignee: Dey Pharma, L.P., Basking Ridge, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,972

(22) Filed: Dec. 23, 2011

(65) Prior Publication Data

US 2012/0309837 A1    Dec. 6, 2012

Related U.S. Application Data

(63) Continuation of application No. 12/785,965, filed on May 24, 2010, now Pat. No. 8,114,912, which is a continuation of application No. 12/340,355, filed on Dec. 19, 2008, now abandoned, which is a continuation of application No. 10/887,785, filed on Jul. 9, 2004, now Pat. No. 7,348,362.

(60) Provisional application No. 60/486,386, filed on Jul. 10, 2003.

(51) Int. Cl.
*A61K 31/167* (2006.01)
*A61P 11/08* (2006.01)

(52) U.S. Cl.
USPC .......................................................... 514/630

(58) Field of Classification Search
USPC ................................................ 514/561, 630
See application file for complete search history.

(56) References Cited

U.S. PATENT DOCUMENTS

| | | |
|---|---|---|
| 3,929,768 A | 12/1975 | Brattsand et al. |
| 3,994,974 A | 11/1976 | Murakami et al. |
| 4,335,121 A | 6/1982 | Phillipps et al. |
| 4,578,221 A | 3/1986 | Phillipps et al. |
| 4,826,689 A | 5/1989 | Violanto |
| 4,985,418 A | 1/1991 | Richards |
| 4,992,474 A | 2/1991 | Skidmore et al. |
| 5,033,252 A | 7/1991 | Carter |
| 5,052,558 A | 10/1991 | Carter |
| 5,126,123 A | 6/1992 | Johnson |
| 5,126,375 A | 6/1992 | Skidmore et al. |
| 5,145,684 A | 9/1992 | Liversidge et al. |
| 5,225,445 A | 7/1993 | Skidmore et al. |
| 5,270,305 A | 12/1993 | Palmer |
| 5,284,656 A | 2/1994 | Platz et al. |
| 5,290,815 A | 3/1994 | Johnson et al. |
| 5,323,907 A | 6/1994 | Kalvelage |
| 5,376,359 A | 12/1994 | Johnson |
| 5,434,304 A | 7/1995 | Trofast et al. |
| 5,510,118 A | 4/1996 | Bosch et al. |
| 5,525,623 A | 6/1996 | Spear et al. |
| 5,552,160 A | 9/1996 | Liversidge et al. |
| 5,556,964 A | 9/1996 | Hofstraat et al. |
| 5,602,110 A | 2/1997 | Drumm et al. |
| 5,637,620 A | 6/1997 | Trofast et al. |
| 5,647,347 A | 7/1997 | Van Oort |
| 5,654,276 A | 8/1997 | Barrett et al. |
| 5,658,549 A | 8/1997 | Akehurst et al. |
| 5,668,110 A | 9/1997 | Barrett et al. |
| 5,674,860 A | 10/1997 | Carling et al. |
| 5,677,280 A | 10/1997 | Barrett et al. |
| 5,677,809 A | 10/1997 | Kadlec |
| 5,683,983 A | 11/1997 | Barrett et al. |
| 5,691,336 A | 11/1997 | Dorn et al. |
| 5,709,884 A | 1/1998 | Trofast et al. |
| 5,733,526 A | 3/1998 | Trevino et al. |
| 5,736,124 A | 4/1998 | Akehurst et al. |
| 5,750,549 A | 5/1998 | Caldwell et al. |
| 5,753,218 A | 5/1998 | Smith et al. |
| 5,780,467 A | 7/1998 | Dorn et al. |
| 5,785,952 A | 7/1998 | Taylor et al. |
| 5,795,564 A | 8/1998 | Aberg et al. |
| 5,823,182 A | 10/1998 | Van Oort |
| 5,849,265 A | 12/1998 | Li-Bovet et al. |
| 5,874,063 A | 2/1999 | Briggner et al. |
| 5,874,481 A | 2/1999 | Weers et al. |
| 5,877,191 A | 3/1999 | Caldwell et al. |
| 5,916,540 A | 6/1999 | Akehurst et al. |
| 5,919,435 A | 7/1999 | Taylor et al. |

(Continued)

FOREIGN PATENT DOCUMENTS

| | | |
|---|---|---|
| DE | 2305092 | 8/1973 |
| DE | 19541689 | 5/1996 |

(Continued)

OTHER PUBLICATIONS

Lachman et al., "Chapter 26: Kinetic Principles and Stability Testing", The Theory and Practice of Industrial Pharmacy, 1986, 3rd Edition.
Whelan, et aL, "Comparison of the Anti-Inflammatory Properties of Formoterol, Salbutamol, and Salmeterol in Guinea-Pig Skin and Lung", British Journal of Pharmacology, 1993. pp. 613-618, 110.
Remington, "Chapter 38: stability of Pharmaceutical Products", The Science and Practice of Pharmacology, 1995, 0 1995, p. 639, 19th Edition.
Rosenborg, et aL, "Mass Balance and Metabolism of [(3)H]Formoterol in Healthy Men after Combined i.v. and Oral Administration-Mimicking Inhalation", Drug Metabolism and Disposition, 1999, pp. 1104-1116, 27(10).
Puigbo, et al., "A New Therapeutical Alternative in the Management of Acute Asthma (Preliminary Report)", Alergia, Asma e Inmunologia, 2000, pp. 73-76 , 11(2).

(Continued)

*Primary Examiner* — Raymond Henley, III
(74) *Attorney, Agent, or Firm* — McDermott Will & Emery LLP

(57) ABSTRACT

Bronchodilating compositions and methods are provided. The compositions are intended for administration as a nebulized aerosol. In certain embodiments, the compositions contain formoterol, or a derivative thereof. Methods for treatment, prevention, or amelioration of one or more symptoms of bronchoconstrictive disorders using the compositions provided herein are also provided.

20 Claims, No Drawings

(56) References Cited

U.S. PATENT DOCUMENTS

| | | |
|---|---|---|
| 5,922,306 A | 7/1999 | Akehurst et al. |
| 5,955,439 A | 9/1999 | Green |
| 5,972,327 A | 10/1999 | Lin et al. |
| 5,972,919 A | 10/1999 | Carling et al. |
| 5,972,920 A | 10/1999 | Seidel |
| 5,980,949 A | 11/1999 | Trofast |
| 5,983,956 A | 11/1999 | Trofast |
| 5,993,781 A | 11/1999 | Snell et al. |
| 5,993,782 A | 11/1999 | Gardner |
| 6,001,336 A | 12/1999 | Gordon |
| 6,004,537 A | 12/1999 | Blondino et al. |
| 6,027,714 A | 2/2000 | Trofast |
| 6,030,604 A | 2/2000 | Trofast |
| 6,040,344 A | 3/2000 | Gao et al. |
| 6,041,777 A | 3/2000 | Faithfull et al. |
| 6,068,833 A | 5/2000 | Aberg et al. |
| 6,068,860 A | 5/2000 | Carlsson et al. |
| 6,071,971 A | 6/2000 | Senanayake |
| 6,112,924 A | 9/2000 | Zhang |
| 6,126,919 A | 10/2000 | Stefely et al. |
| 6,136,603 A | 10/2000 | Dean et al. |
| 6,150,418 A | 11/2000 | Hochrainer et al. |
| 6,153,173 A | 11/2000 | Sapsford et al. |
| 6,183,782 B1 | 2/2001 | Hallworth |
| 6,199,607 B1 | 3/2001 | Trofast |
| 6,200,549 B1 | 3/2001 | Akehurst et al. |
| 6,221,398 B1 | 4/2001 | Jakupovic et al. |
| 6,235,725 B1 | 5/2001 | Ahmed |
| 6,241,969 B1 | 6/2001 | Saidi et al. |
| 6,251,368 B1 | 6/2001 | Akehurst et al. |
| 6,253,762 B1 | 7/2001 | Britto |
| 6,261,539 B1 | 7/2001 | Adjei et al. |
| 6,287,540 B1 | 9/2001 | Trofast |
| 6,287,693 B1 | 9/2001 | Savoir et al. |
| 6,291,445 B1 | 9/2001 | Nilsson et al. |
| 6,303,145 B2 | 10/2001 | Jerussi et al. |
| 6,306,368 B1 | 10/2001 | Taylor et al. |
| 6,306,369 B1 | 10/2001 | Akehurst et al. |
| 6,309,623 B1 | 10/2001 | Weers et al. |
| 6,309,624 B1 | 10/2001 | Sapsford et al. |
| 6,365,190 B1 | 4/2002 | Gordon et al. |
| 6,369,115 B1 | 4/2002 | Ward |
| 6,406,718 B1 | 6/2002 | Cooper |
| 6,413,496 B1 | 7/2002 | Goodman et al. |
| 6,416,742 B1 | 7/2002 | Stefely et al. |
| 6,423,298 B2 | 7/2002 | McNamara et al. |
| 6,448,296 B2 | 9/2002 | Yasueda et al. |
| 6,451,287 B1 | 9/2002 | Desimone et al. |
| 6,461,591 B1 | 10/2002 | Keller |
| 6,464,958 B1 | 10/2002 | Bernini et al. |
| 6,475,467 B1 | 11/2002 | Keller et al. |
| 6,479,035 B1 | 11/2002 | Cripps et al. |
| 6,481,435 B2 | 11/2002 | Hochrainer et al. |
| 6,482,390 B1 | 11/2002 | Hiscocks et al. |
| 6,598,603 B1 | 7/2003 | Andersson et al. |
| 6,632,842 B2 | 10/2003 | Chaudry et al. |
| 6,667,344 B2 | 12/2003 | Banerjee et al. |
| 6,686,346 B2 | 2/2004 | Nilsson et al. |
| 6,702,997 B2 | 3/2004 | Chaudry et al. |
| 6,814,953 B2 | 11/2004 | Banerjee et al. |
| 6,816,510 B1 | 11/2004 | Banerjee |
| 7,070,800 B2 | 7/2006 | Bechtold-Peters et al. |
| 7,348,362 B2 | 3/2008 | Banerjee et al. |
| 7,462,645 B2 | 12/2008 | Chaudry et al. |
| 7,465,756 B2 | 12/2008 | Chaudry et al. |
| 7,473,710 B2 | 1/2009 | Chaudry et al. |
| 7,541,385 B2 | 6/2009 | Chaudry et al. |
| 2001/0024641 A1 | 9/2001 | Yang |
| 2002/0032149 A1 | 3/2002 | Kensey |
| 2002/0042404 A1 | 4/2002 | Bauer et al. |
| 2002/0061835 A1 | 5/2002 | Kensey |
| 2002/0081266 A1 | 6/2002 | Woolfe et al. |
| 2002/0099013 A1 | 7/2002 | Piccariello et al. |
| 2002/0103260 A1 | 8/2002 | Clarke et al. |
| 2002/0151597 A1 | 10/2002 | Banerjee et al. |
| 2002/0151598 A1 | 10/2002 | Banerjee et al. |
| 2002/0183293 A1 | 12/2002 | Banerjee et al. |
| 2003/0055026 A1 | 3/2003 | Banerjee et al. |
| 2003/0109510 A1 | 6/2003 | Gavin |
| 2003/0124063 A1 | 7/2003 | Chaudry et al. |
| 2004/0023935 A1 | 2/2004 | Banerjee et al. |
| 2004/0109826 A1 | 6/2004 | Malladi et al. |
| 2004/0110845 A1 | 6/2004 | Malladi et al. |
| 2005/0009923 A1 | 1/2005 | Banerjee et al. |
| 2007/0160541 A1 | 7/2007 | Chaudry et al. |
| 2007/0166235 A1 | 7/2007 | Banerjee et al. |
| 2007/0166236 A1 | 7/2007 | Banerjee et al. |
| 2007/0166240 A1 | 7/2007 | Banerjee et al. |

FOREIGN PATENT DOCUMENTS

| | | |
|---|---|---|
| DE | 19541689 A1 | 5/1996 |
| DE | 19835346 | 2/2000 |
| DE | 19835346 A1 | 2/2000 |
| DE | 19847970 | 4/2000 |
| DE | 19847970 A1 | 4/2000 |
| EP | 0370632 | 5/1990 |
| EP | 0370632 A1 | 5/1990 |
| EP | 0616525 | 9/1994 |
| EP | 0616525 B1 | 9/1995 |
| EP | 1157689 | 11/2001 |
| EP | 1157689 A1 | 11/2001 |
| EP | 1 229 034 | 8/2002 |
| EP | 1229034 A1 | 8/2002 |
| EP | 1 236 467 | 9/2002 |
| EP | 1236467 A1 | 9/2002 |
| WO | WO-91/04984 A1 | 4/1991 |
| WO | WO-92/05147 A1 | 4/1992 |
| WO | WO 93/11773 | 6/1993 |
| WO | WO-93/11773 A1 | 6/1993 |
| WO | WO 95/05805 | 3/1995 |
| WO | WO-95/05805 A1 | 3/1995 |
| WO | WO 95/31964 | 11/1995 |
| WO | WO-95/31964 A1 | 11/1995 |
| WO | WO 96/18384 | 6/1996 |
| WO | WO-96/18384 A1 | 6/1996 |
| WO | WO 96/19198 | 6/1996 |
| WO | WO-96/19198 A1 | 6/1996 |
| WO | WO 96/19968 | 7/1996 |
| WO | WO-96/19968 A1 | 7/1996 |
| WO | WO 96/32095 | 10/1996 |
| WO | WO-96/32095 A1 | 10/1996 |
| WO | WO 97/47286 | 12/1997 |
| WO | WO-97/47286 A1 | 12/1997 |
| WO | WO 98/05302 | 2/1998 |
| WO | WO-98/05302 A1 | 2/1998 |
| WO | WO 98/15280 | 4/1998 |
| WO | WO-98/15280 A1 | 4/1998 |
| WO | WO-98/24450 A1 | 6/1998 |
| WO | WO-98/31350 A1 | 7/1998 |
| WO | WO 98/31351 | 7/1998 |
| WO | WO-98/31351 A1 | 7/1998 |
| WO | WO 98/31352 | 7/1998 |
| WO | WO-98/31352 A1 | 7/1998 |
| WO | WO 98/34595 | 8/1998 |
| WO | WO-98/34595 A1 | 8/1998 |
| WO | WO 98/34596 | 8/1998 |
| WO | WO-98/34596 A2 | 8/1998 |
| WO | WO 98/41193 | 9/1998 |
| WO | WO-98/41193 A1 | 9/1998 |
| WO | WO-98/52544 A1 | 11/1998 |
| WO | WO-99/00134 A1 | 1/1999 |
| WO | WO-99/15182 A1 | 4/1999 |
| WO | WO-99/25359 A1 | 5/1999 |
| WO | WO-99/30703 A1 | 6/1999 |
| WO | WO-99/36095 A1 | 7/1999 |
| WO | WO-99/40939 A1 | 8/1999 |
| WO | WO-99/48476 A1 | 9/1999 |
| WO | WO-99/53926 A1 | 10/1999 |
| WO | WO-99/61003 | 12/1999 |
| WO | WO-99/61003 A1 | 12/1999 |
| WO | WO-99/64014 A1 | 12/1999 |
| WO | WO-99/65464 | 12/1999 |
| WO | WO-99/65464 A1 | 12/1999 |

(56) References Cited

FOREIGN PATENT DOCUMENTS

| WO | WO-00/00181 | 1/2000 |
|---|---|---|
| WO | WO-00/06121 | 2/2000 |
| WO | WO-00/07567 | 2/2000 |
| WO | WO-00/16814 | 3/2000 |
| WO | WO-00/23037 | 4/2000 |
| WO | WO-00/23065 | 4/2000 |
| WO | WO-00/23065 A2 | 4/2000 |
| WO | WO-00/28979 | 5/2000 |
| WO | WO-00/030612 | 6/2000 |
| WO | WO-00/33892 | 6/2000 |
| WO | WO-00/42700 | 7/2000 |
| WO | WO-01/78735 | 10/2001 |
| WO | WO-01/89492 | 11/2001 |
| WO | WO-02/11803 A1 | 2/2002 |
| WO | WO-02/28368 | 4/2002 |
| WO | WO-02/28368 A1 | 4/2002 |
| WO | WO-02/30394 A2 | 4/2002 |
| WO | WO-02/34237 A1 | 5/2002 |
| WO | WO-02/38107 A2 | 5/2002 |
| WO | WO-2005/007142 A2 | 1/2005 |

OTHER PUBLICATIONS

Maesen, et al., "Formoterol Suspension Aerosol. Comparison with Formoterol Solution Aerosol for 12 Weeks in Asthmatic Patients", Chest, 1992, pp. 1544-1549, 102.

Barlow et al, "An Update of its Pharmicological Properties and Therapeutic Efficacy in the Management of Asthma," Drugs, 55(2):303-322 {1998).

Becker et al "Formoterol, 11 new long-acting selective b2-adrenergic receptor aganist: Double-blind comparison with salbutarnol and placebo in children with asthma" J. Allergy Clin. Immunol. 84:891-895 (1989).

Campbell et al, "A comparison of the efficacy of long-acting B2.agonists:eformeterol via Tutbohaler(R) and salrneterol via pressurized metered dose inhaler or Accuhaler(R), in mild to moderate asthmatics," Respiratory Medicine 93:236-244 (1999).

Campestrini el al., "Automated and sensitive method for the determination of Formoterol in hunman plasma by high-performance liquid chromatography and electrochemical detection," Journal of Chromatography B 704:221.229 (1997).

Dellamary et al., "Hollow Porous Particles in Meterd Dose Inhalers," Pharmaceutical Research, 17{2}:168-174 {2000).

Derwent #000971705, , WPI Ace. No. 1973..48969U/I97335 citing German Patent Application No. DE 2305092 A. "Alpha-aminomethybenzyl alcohol derives. -prepd, by redn of corresepond-ing protected derives."

Derwent #010743444. WPI Acc No. 1996-240399/199625 for German Patent Application DE 19541689, "Medicament contg. ciclesonid and beta2-sympathomimetic for treating chronic obstructive respiratory disease".

Derwent #012030009. EPI Acc No. 1998-446919-199838 for PCT Patent Application WO 98/34595, "Pressurised liquid aerosol propellant for pharmacreutical inhalers contains carbondioxide and hydro-fluoroalkane; give more consistent dosing and a better particle size spectrum".

Derwent #013011051, WPI Acc No. 2000.182903/200016 for PCT Patent Application WO 00/06121, "Aerosol propellant comprising dinitrogen monoxide and hydrofluoroalkane and optionally containing a pharmaceutically active substance".

Derwent #013023586, WPI Acc No. 2000-1954371200017, for PCT Patent Application WO 00/07567, "Aerosol formulation of rdrug administration, containing small amount of cromoglycate or medocromil salt as drug carrier to improve dispersion stability and accuracy of dosing".

Derwent# 013024375, WPI Acc No. 2000-1962226/200018 for German Patent Application DE 19835346, Two-part drug capsule for use in powder inhalers is formed from hydrophobic plastics, preferably high density polyethylene'.

Derwent#013227165, WPI Acc No. 2000-399639/200034, for per PCT Application WO 00/28979, "Use ofmagnesiurn state for stabilization of dry powder inhalation formlations to improve ersistance to moisture".

Derwenl#013790372, WPI Acc No. 2001-27458/200129, for PCT Patent Application WO 01/22956, "Drug combination of soft steroid and beta-2-adrenoreceptor, agonist, administered by inhalation for effective treatment of respiratory of allergic diseases, e.g, asthma".

Derwent#014808338, WPI Acc No. 2001-6290441200168, fot PCTPatcnt Application WO 02/060533. "Medicament containing a betamimetic and an oxitropium salt useful for the treatment of respiratory disorders with reduced side effects".

Derwent#014806787, WPI Acc No. 2002-6374931200269. for PCT Patent Application Wo 021060532, "Medicament containing a betamimetic and an ipratropium salt useful for the treatment of respiratory disorders with reduced side effects".

Eidkelberg et al., "Ligand—indepenrlent Activation of the Glucocorticoid Receptor by b2-Adrenergic Receptor Agonists in Primary Human Lung Fibroblasts and Bascular Smooth Muscle Cells," J. Biol. Chem.. 272(2}:1005.1010 (1999).

Ekstrom et al., "Low-dose formoterol Turbuhaler(R) (Oxis(R)) b.i-d., a 3-month placebo-controlled comparison with terbutaline (q.i.d,)," Respiratory Medicine 92.: 1040-1045 (1998).

Flovent.' Glaxo Wellcome Inc., Physicians' Desk Reference, 541.': Ed., {2000), pp. 1186-1189.

Greening. et al, "Added salmeterol versus higher-dose corticosteroid in asthma patients with symptoms on existing inhaled corticosteroid." The Lancet: 344:219-244 (1994).

Grootendorst et al, "Effect of orol prednisolone on the bronchoprotective effect of formoterol in patient with persistent asthma," Eur. Respir. J. 17:374-379 (2001).

Hardman et al. (Eds.), Goodman Gilman's:; The Pharmacological Basis of Therapeutics, 1996, p. 665.

Ida "Comparison of the Action of BD 40A lind some Other b-Adrenoceptor Stimulants on the Isola1ed Trachea and Atria of the Guinea Pig" Arzneim.-Forsch. (Drug Res) 26:839-842 (1976).

Ida "Cardiorespiratory Activities of 3-Formylamino-4-hydroxy~a-(N-i-methyl-2-p-methoxypbenethylaminomethyl)benzylalcoho!-hemifumarate (BD 40A) and some other b-Adrenoceptor Stimulants in Conscious Guinea Pigs" Arznem-Forsch. (Drug Res.) 26:1337-1340 (1976).

Ida, Hisashi, "Pharmacology of Formeterol, (aRS}-3-formamido-4-hydroxy-a-[[[ (aRS)-p-methoxy-a-methylphenethyl]amino]methyl]benzyl) alcohol fumatate dehydrate {ED 40A)," Oyo Yakui 21(2);201-210 (1981).

Ito et al "Glucocortoid Receptor Recruitment of Histone Deacetylase 2 Inhibits Interleukin-1b-Induced Histone H4 Acetylation on Lysines 8 and 12," Molecular and Cellular Biology 20{18}:6892-6903 (2000).

Ito el al., "p65-ac:tivllted Histone Aeetyltransferase Activity is Repressed by GlucoconicolDs," J. Biol. Chern. 276(31):30208-30215 (2001).

Kmnimura et al. "Quantitative Determination of the b-adrenoceptor stimulan Formeterol in Urine by Gas Chromatograph Mass Sptectrometry" J. Chrom. 229:337-345(1982).

Kaumann e.! al., "Direct Labelling ofmyocllrdial Bl-adrenorecep-tors~ Comparison of Binding Affmity of3H-(-}-b~prolo1 with its blocking potency," Arch. Phann. 33]:]7-39 (1985).

Korn et al, "Effects of formeterol and budesonide on GM-CSF and IL-8 secretion by Triggerd human bronchial epithelial cells," Eur. Respir. J. 17:1010-1077 (2001).

Lebecque et al. "Effet dl'une dose unique de formoterol par voie daerosol•doseur chez l'enfani asthmatique" Rev. Maj. Respi. 11 :47-50 (1994).

Lecaillon elal., "Parrnacokinetics and tolerability of formoterol in healthy volunteers after a single high dose of Foradil dry powder Inhalation via aerolizer (TM)," Eur. J. Ciin. Pharm. 55;131-139(1999).

Leckie et al, "Novel Therpy of COPD," Expert Opin. Investig Drugs 9(1):3-23(2000).

Ball, D.I.. et al., "Salmeterol, a novel, long-acting $\beta_2$-adrenoceptor agonist: characterization of pharmacological activity in vitro and in vivo" (1991), Br. J. Pharmacol. 104, 665-671.

Barnes, "Scientific rationale for inhaled combination therapy with long-acting b2-agonists and corticosteroids," Eur. Respir. J., 19:182-191 (2002).

(56) References Cited

OTHER PUBLICATIONS

Berger, "Aerosol Devices and Asthma Therapy" Current Drug Delivery, 2009, 6, 38-49.
Cazzola et al., "Long-Acting b2-Agonists in the Treatment of Acute Exacerbations of COPD," *Clin. Drug Invest.*, 22(6): 168-174 (2002).
Derwent WPI Acc No. 2000-304726 for PCT Patent Application WO 00123037, "Stable concentrated liquid formulation of inhalable drug, e.g. formoterol or salbutamol, in solution or suspension medium, used after dilution for treatment of respiratory disorders by inhalation", 2000.
Dolovich, "Device Selection and Outcomes of Aerosol Therapy: Evidence-Based Guidelines" Chest 2005, 127, 335-371.
Geller, Comparing Clinical Features of the Nebulizer, Metered-Dose Inhaler, and Dry Powder Inhaler, Respiratory Care, Oct. 2005, vol. 50 No. 10 pp. 1313-1322.
Greening et al., "Added salmeterol versus higher-dose corticosteroid in asthma patients with symptoms on existing inhaled corticosteroid," *The Lancet*, 344:219-244 (1994).
Hess, Respiratory Care, Jun. 2008, vol. 53 No. 6, 699-725.
Hess, Aerosol delivery during mechanical ventilation, Minerva Anestisiologica, vol. 68 No. 5 (2002) pp. 321-325.
Ikeda, at al., Comparison of the Bronchodilator Effects of Salbutamol Delivered via a Metered-Dose Inhaler with Spacer, a Dry-Powder Inhaler, and a Jet Nebulizer in Patients with Chronic Obstructive Pulmonary Disease, Respiration (1999) 66:119-123.
Kibbe, A.H. (ed.), Handbook of Pharmaceutical Excipients, 3rd Ed., "Citric Acid Monohydrate," pp. 140-142 (2000).
Korn et al., "Effects of formoterol and budesonide on GM-CSF and IL-8 secretion by triggered human bronchial epithelial cells," *Eur. Respir. J.*, 17:1070-1077 (2001).
On-line Orange Book Listing for Dey's "Perforomist," formoterol for nebulization.
Rau, Practical Problems With Aerosol Therapy in COPD, Respiratory Care, Feb. 2006 vol. 51 No. 2, pp. 158-172.
Sasaki et al., "Desposition and metabolism of formoterol fumarate, a new bronchodilator, in rats and dogs," *Xenobiotic*, vol. 12, pp. 803-809 (1998).
Siegel, F., "Tonicity, osmoticity, osmolality and osmolarity" *Remington's Pharmaceutical Sciences*, Seventeenth Edition, Chaprter 80, pp. 1455-1472 (1985).
U.S. Appl. No. 09/887,496: Advisory Action dated Oct. 8, 2003, 3 pages.
U.S. Appl. No. 09/887,496: Final Office Action dated May 20, 2003, 9 pages.
U.S. Appl. No. 09/887,496: Final Office Action dated Jan. 11, 2005, 15 pages.
U.S. Appl. No. 09/887,496: Final Office Action dated Mar. 13, 2007, 15 pages.
U.S. Appl. No. 09/887,496: Final Office Action dated Jun. 4, 2008, 17 pages.
U.S. Appl. No. 09/887,496: Final Office Action dated Jul. 22, 2009, 19 pages.
U.S. Appl. No. 09/887,496: Non-Final Office Action dated Apr. 24, 2002, 7 pages.
U.S. Appl. No. 09/887,496: Non-Final Office Action dated Dec. 18, 2002, 9 pages.
U.S. Appl. No. 09/887,496: Non-Final Office Action dated Jul. 1, 2004, 16 pages.
U.S. Appl. No. 09/887,496: Non-Final Office Action dated Jul. 5, 2006, 15 pages.
U.S. Appl. No. 09/887,496: Non-Final Office Action dated Aug. 27, 2007, 15 pages.
U.S. Appl. No. 09/887,496: Non-Final Office Action dated Oct. 28, 2008, 21 pages.
U.S. Appl. No. 09/887,496: Supplemental Advisory Action dated Dec. 19, 2003, 2 pages.
U.S. Appl. No. 10/145,978: Final Office Action dated May 12, 2004, 8 pages.
U.S. Appl. No. 10/145,978: Final Office Action dated Jan. 3, 2008, 11 pages.
U.S. Appl. No. 10/145,978: Final Office Action dated May 26, 2009, 11 pages.
U.S. Appl. No. 10/145,978: Interview Summary/Advisory Action dated May 13, 2008, 4 pages.
U.S. Appl. No. 10/145,978: Non-Final Office Action dated Aug. 26, 2003, 8 pages.
U.S. Appl. No. 10/145,978: Non-Final Office Action dated Sep. 28, 2005, 10 pages.
U.S. Appl. No. 10/145,978: Non-Final Office Action dated Jun. 11, 2007, 10 pages.
U.S. Appl. No. 10/145,978: Non-Final Office Action dated Aug. 20, 2008, 17 pages.
U.S. Patent No. 7,348,362 (U.S. Appl. No. 10/887,785): Non-Final Office Action dated Jun. 14, 2007, 7 pages.
U.S. Patent No. 7,462,645 (U.S. Appl. No. 11/688,429): Non-Final Office Action dated Oct. 18, 2007, 7 pages.
U.S. Patent No. 7,465,756 (U.S. Appl. No. 11/688,436): Non-Final Office Action dated Oct. 18, 2007, 7 pages.
U.S. Patent No. 7,473,710 (U.S. Appl. No. 11/688,450): Non-Final Office Action dated Oct. 17, 2007, 7 pages.
U.S. Patent No. 7,541,385 (U.S. Appl. No. 11/688,463): Non-Final Office Action dated Oct. 17, 2007, 7 pages.
U.S. Appl. No. 10/145,978: Final Office Action dated May 22, 2006, 11 pages.
Stenesh, J., Dictionary of Biochemistry and Molecular Biology (2d ed. 1989), p. 364.
Sterns, R.H. et al., Salt and Water: read the package insert, Q.J. Med. (2003), 96:549-552.
Roy, R. et al., Buffer Standards for the Physiological pH of Zwitterionic Compounds, MOBS and TABS from 5 to 55° C., J. Solution Chemistry (vol. 33, No. 10, Oct. 2004), pp. 119-1211.
Non-Final Office Action in Reexaminatin No. 90/010,489 dated Jun. 8, 2010 (43 pages).
Non-Final Office Action Dated May 15, 2009 in Reexaminatin No. 90/010,489.
Final Office Action in Reexamination No. 90/010,489 dated May 15, 2009 (18 pages).
Non-Final Office Action in Reexamination No. 09/010,488 dated (39 pages).
Final Office Action in Reexamination No. 90/0101,488 dated May 19, 2011 (14 pages).
Non-Final Office Action Dated Jun. 8, 2010 in Reexaminatin No. 90/010,489 (43 pages).
Non Final Office Action in Reexamination No. 09/010,488 dated (39 pages).
Final Office Action in Reexamination No. 90/0101.488 dated May 19, 2011 (14 pages).
Lemoine et al, "Direct labeling of B2-adrenorecepters. Comparison of binding potency of 3H-1C1 118,551 and blocking potency of 1C1 118,551," Arch. Pharm. 331:40-51 {1985}.
Lipworth et al, "Effects of Treatment with Formoterol on Bronchoprotection against Methacholine," Am.J. Med.104:431-438(1998).
Lotvalll et al.. "Similar broncodilation with Formoterol delivered by Aerolizer or Turbuhaler," Can. Respir. J. 6(5):412-416 (1999).
Maesen et al "The Effect of Maximal Doses of Formoterol and Salbutarnol from a Metered Dose Inhaler on Pulse Rates, ECG, and Serum Potassium Concentrations" Chest 99:1367-1373 (1991).
Maesen et al "Formoterol as Dry Powder Inhnlation" Chest 101:1376-1381 (1992).
Malolepszy et al., "Safety of Q1 Formoterol Turbuhaler(TM) at cumulative dose of 90 mg in patients with acute bronchial obstruction," Eur. Respir-. J. 8~928-934 {2001}.
Miller et al, "Chronic Effects of the Novel Glucocorticosoid RPR 106541 Administered to Beagle Dogs by Inhalation" Toxic. Path. 28:226-236 (2000).
Murase et al. "New b-Adrenoreceptor Stimulatants. Studies on 3•Acylamino-4-hydroxy-a-(N-substituted aminomethyl)benzyl Alcohols" Chern Pharm. Bu11. 26;1368-1377 (1977).
Nielsen et al, "Flow-dependent effect of formoterol dry powder inhaled from the Aerolizer(R)," Eur, Respir. J. 10:2105-2109 (1997).

(56) References Cited

OTHER PUBLICATIONS

Nightingale et al, "Differential Effect of Formoterol on Adenosine Monophophate and Histamine Reactivity in Asthma," Am. J. Respir. Crit. Care Mad. 159 1786-1790 (1999).

Nogrady. T., (Editor). Medicinal Chemistry: A Biochemical Approach. Oxford University Press, New York. pp. 388-392 (1985).

O'Connor "Combination Therapy," Pulm. Pharm. & Ther 11 :379-399 (1998).

Oddera et al,, "Salmeterol Enhances the Inhibitory Activity of Dexamethaasone on Allergen-Induced Blood Mononuclear Cell Activation," Respiration 65:199-204 (1998).

Package Insert for Advair{TM) Discus http://1b.a-files.netl/PackageInsert?Advair.htm (Accessed on Sep. 26, 2002) (Copyright, 1999 Glaxo Wellcorne Inc.).

Palmqvist et al, "Inhaled dry-powder formeterol and almeterol in asthmatic patients; onset of action, duraton of effect and potency" Eur. Respir. J. 10:2484-2489 (1997).

Palmqvist et al., "Onset of Bronchodilation of Budesonide/formoterol vs. Salmeterol/Fluticasone in Single Inhalers," Pulm. Pharm. & Ther. 14:29-34 (2001).

Pang et al., "Regulation of TNF-a-induced cotaxin release from cultured human airway smooth muscle cells by b2-agonists and corticoseroids," FASEB J, 15:261-269 (2001).

Pang et al., Synergisltc Inhibition by b2-.Agonists and Corticosteroids on Tumor Necrosis Facltor-a-Induced Interleukin-8 Release from Cultured Human Airway Smooth-Musde Cells:' Am, J. Respir- Cell Mol. Bio. 23:79-85 (2000).

Pauwels et al.. "Effect of Inhaled Formeterol and Budesonide on Exacerbations of Asthma," The New England J. Med. 337(20): 1405-1411 (1997).

Physicians' Desk Reference: PDR, Oradell. J J.: Medical Economics Co., pp. 535-537, : 480-4&2, 2828-2829 (2000).

Rico-Mendez et al, "Formoterol en polvo seco, dos veces al dia versus salbutamol aerosol, coatro veces al dia, en pacientes con asma estable," Revista Alergia Mexico XLVI(5):130-135 (1999).

Ringdal et al, "Onset and duration of action of single doses of formeterol inhaled via Turbuhaler(R)." Resp. Med. 92:1017~1021 (1998).

Sasaki et al "Desposition and metabolism of formeterol fumarate, a new bronchoddilatof, in rats and dogs" Xenobiotic 12:803-832 (1982).

Scheen Pharma•Clinics le Medicament du Mois le formeterol (Oxis Turbohaler) Rev. Med. Liege 53:11:715-718 (1998).

Schreurs et al, "A dose. response study vlith formeterol Turbuhaler(R) as maintenance therapy in asthmatic patients," Eur. Respir. J. 9:1678-1683:; (1996).

Seberova et al. "Oxis(R) (formeterol given by Turbuhaler(R)) showed as rapid an onset of action as salbutamol given by II pMDI," Rasp. Med. 94:60Nill {20GO).

Selroos et al, "Delivery Deviceds for Inhaled Asthma Medication," Clin. Immunolher. 6:273-299 (1996).

Seldon et al. "AlbuterolDoes Not Anlagunize the InbibitoryEffect o Dexame1hasnne on Monocyte Cylokine Release.," Am, J, Respir. Grit. CnreMed. 157:80J . . . s09(1998).

Silvestri et al, "Fluticasone and salmeterol donteguJate in vitro, fibroblast proliferation and JCAM-I or H-CAM expression," Eru. Respir. J. 18:139-145 (2001).

Skold et al., "Glucorticoids Augment Fibroblast-Mediated Contration of Collagen Gels by Inhjbition of Endogenous PGE Production," Proc;. Assoc. Am. Phys. 111(3}:239-258 (1999).

Smaldone et al, "Budesonide Inhalation Suspension in Chemically Compatable with Other Nebulizing Formulations" Chest 119(4)Suppl: 98S (2000).

Sovijarvi et al. "Preventive Effects of Inhaled Formoterol and Salbutamol on Histamine-Induced Bronchoconstriction—A Placebo-Controlled Study" Respiration 59:Z79-282 (1992).

Stevens et al. "Use of the Steroid Derivative RPR 106541 in Combination with Site-Directed Mutagenesis for Enhanced Cytochrome P-450 3A4 Structure/Funtion Analysis" J. Pharma. Exp. Ther, 290:594-602 (1999).

Stewart et aL,"Acute formoterol administration has no argogenic effect in Inonasthmatic athletes," Medicine & Science in Sports & Exercise 34(2):213-217 (2002).

Tomioka et al., "Anti-Allergic Actiivities of the b-Adrenoreceptor Stimulant Formoterol (BD-40A)," Arch. Int. Pharmacodyn. 250 279-292 (1981).

Totterman et al., "Tolerability to high doses of formoterol terbutaline via Turbulhaler(R) for 3 days in stable asthmatic patients," Eur. Respir. J. 12:573-579 (1998).

Ullman et al., "Formoterol inhaled as dry powder or via pressurized meterd•dose; Inhaler in a curnulative dose-response study," Allergy 51 :745-748 (1996).

Van den Berg et al. "Evaluation of different doses of Formoterol from a newly developed powder inhalation device in asthmatic patients" Fundam. Clin. Pharmacol. 9:593-603 (1995).

Vianna et al., "Bronchodilators and Corticosteroids in the Treatment of Asthma," Drugs of Today 34(3):203-223 (1998).

Wallin et al. "Time course and duration of bronchodilatation with forrnoterol dry powder in patients with stable asthma" Thorax 48:611-614 (1993).

Warne, The discovery and clinical development of RPR 106541: an airway-selective steroid for the treatment of asthma:; Emergjng Drugs 5(2):231-239 (2000).

Wilding et al., "Effect of long term treatment with Salmeterol on asthma control: a double blind, randomized crossover study," British Med. J. 314:1441-1446 (1997).

Woolcock et al, "Comparison of Addition of Salmeterol to Inhaled Steroids with Doubling of the Dose of Inhaled Steroids," Am. J. Res.pir. Cot. Care Med. 153: 1431•1488(1996).

Yokoi et al "The Development of a Radioimmunoassay for Formoterol" Life Sciences. 33:1665-1612 (1983).

Yoshida et al., "Acute; Subacute and Chronic Ioxidty Studies of a Bronchodialator. Formoterol Fumarate (BD 40)" Oyo Yakuri, 26(5), 811-29 {1983}.

Derwent WPI Acc No. 2000-304126 for PCT Patent Application WO 00/23037, "Stable concentrated liquid fomulation of inhalable drug, e.g. formoterol or salbutamol, in solution or suspension medium, used after dilution for treatment of respiratory disorders by inhalation".

Bedi "Inhaled Corticosteroids in COPD "Indian J Chest Allied Sci 2005; 47: 243-244.

Nials, et al., "Effects of B~adrenoceptor agooists in human bronchial smooth muscle". Br. J. Pharmacol.

Nials, et al, "Formoterol on airway smooth muscle and human lung mast cells . . . ", European Journal of Pharmacology, 1994,251: 127-135.

Mohammed, S.P. et al., "Duration of action of inhaled vs Intravenous β2-adrenoceptor .. " Pulmonary Pharmacology & Theraeutics, 2000, 13:287-292.

*Dey v. Sepracor*; 1:07-cv-2353; Complaint.

*Dey v. Sepracor*; 1:07-cv-2353; Answer and Counterclaims.

*Dey v. Sepracor*, 1:07-cv-2353; Reply to Counterclaims.

*Dey v. Sepracor*, 1:07-cv-2353; Answer to Additional Claims.

BRONCHODILATING BETA-AGONIST COMPOSITIONS AND METHODS

RELATED APPLICATIONS

This application is a continuation of U.S. patent application Ser. No. 12/785,965, filed May 24, 2010, issued as U.S. Pat. No. 8,114,912, which is a continuation of U.S. patent application Ser. No. 12/340,355, filed Dec. 19, 2008, now abandoned, which is a continuation of U.S. patent application Ser. No. 10/887,785, filed Jul. 9, 2004, issued as U.S. Pat. No. 7,348,362, which in turn claims priority under 35 U.S.C. §119(e) to U.S. Provisional Patent Application No. 60/486,386, filed Jul. 10, 2003, entitled "BRONCHODILATING β-AGONIST COMPOSITIONS AND METHODS." The disclosure of each of the above-referenced applications is incorporated by reference herein in its entirety.

FIELD

Compositions and methods are provided relating to treatment, prevention, or amelioration of one or more symptoms of bronchoconstrictive disorders. In particular, the compositions and methods herein include formoterol, and/or derivatives thereof. The compositions are propellant-free, sterile unit dose or multidose inhalation solutions intended for administration via nebulization.

BACKGROUND

Bronchoconstrictive disorders affect millions worldwide. Such disorders include asthma (including bronchial asthma, allergic asthma and intrinsic asthma, e.g., late asthma and airway hyper-responsiveness), chronic bronchitis and other chronic obstructive pulmonary diseases. Compounds having $β_2$-adrenoreceptor agonist activity have been developed to treat these conditions. Such compounds include, but are not limited to, Albuterol ($α^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-dimethylethyl)amino)-methyl)benzenemethanol); Fenoterol (5-(1-hydroxy-2-((2-(4-hydroxyphenyl)-1-methylethyl)-amino)ethyl)-1,3-benzenediol); Formoterol (2-hydroxy-5-((1RS)-1-hydroxy-2-(((1RS)-2-(p-methoxyphenyl)-1-methylethyl)amino) ethyl)formanilide); (R,R)-Formoterol; Desformoterol ((R,R) or (S,S)-3-amino-4-hydroxy-α-(((2-(4-methoxyphenyl)-1-ethylethyl)amino)methyl)-benzene-methanol); Hexoprenaline (4,4'-(1,6-hexanediyl)-bis(imino-(1-hydroxy-2,1-ethanc-diyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino) ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy) hexyl)-amino)methyl)benzenemethanol); Pirbuterol ($α^6$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxy-phenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$α^1$-(((1,1-dimethylethyl)amino)methyl)-4-hydroxy-1,3-benzenedimethanol); (R)-Salbutamol; Salmeterol ((−)-4-hydroxy-$α^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)-methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

These compounds are typically formulated for inhalation therapy. Aqueous or liquid formulations are preferred over solid formulations. Powdered formulations are more difficult to administer, particularly to the young and elderly who are most often the patients in need of such therapy. Compounds, such as formoterol are not adequately stable in aqueous solutions to be formulated as liquids. Hence there is a need for formulations of compounds, such as formoterol, in a form that can be conveniently administered and that are stable for extended periods of time.

SUMMARY

Compositions and methods for treatment, prevention, or amelioration of one or more symptoms of bronchoconstrictive disorders are provided. The compositions provided herein are stable solutions of a bronchodilating agent, or a derivative thereof, in a pharmacologically suitable fluid that contains water, that are stable during long term storage. The compositions are suitable for direct administration to a subject in need thereof. Pharmacologically suitable fluids include, but are not limited to, polar fluids, including protic fluids. In certain embodiments herein, the compositions are aqueous solutions.

The compositions provided herein possess an estimated shelf-life of greater than 1, 2 or 3 months usage time at 25° C. and greater than or equal to 1, 2 or 3 years storage time at 5° C. In certain of these embodiments, using Arrhenius kinetics, >80% or >85% or >90% or >95% estimated bronchodilating agent remains after such storage. These compositions are particularly useful, for administration via nebulization. In certain embodiments herein, the subject is a mammal. In other embodiments, the subject is a human.

The compositions provided herein are formulated to remain stable over a relatively long period of time. For example, the compositions provided herein are stored between −15° C. and 25° C., or between 2° C. and 8° C., and remain stable for the desired time. In one embodiment, the compositions are stored at 5° C. In other embodiment, the compositions are stored at 25° C.

Among the bronchodilating agents for use herein are Albuterol ($α^1$-(((1,1-dimethylethyl)-amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino)-methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-dimethylethyl)amino)methyl)benzenemethanol); Fenoterol (5-(1-hydroxy-2-((2-(4-hydroxyphenyl)-1-methylethyl)amino)ethyl)-1,3- benzenediol); Formoterol (2-hydroxy-5-((1RS)-1-hydroxy-2-(((1RS)-2-(p-methoxyphenyl)-1-methylethyl)amino)ethyl)-formanilide); (R,R)-Formoterol; (S,S)-Formoterol; Desformoterol ((R,R) or (S,S)-3-amino-4-hydroxy-α-(((2-(4-methoxyphenyl)-1-methylethyl)amino)methyl)benzenemethanol); Hexoprenaline (4,4'-(1,6-hexanediyl)-bis(imino(1-hydroxy-2,1-ethane-diyl)-))bis-1,2-benzenediol); Isoetharine (4-(1-hydroxy-2-((1-methylethyl)amino)-butyl)-1,2-benzenediol); Isoprenaline (4-(1-hydroxy-2-((1-methylethyl)amino)ethyl)-1,2-benzenediol); Metaproterenol (5-(1-hydroxy-2-((1-methylethyl)-amino)ethyl)-1,3-benzenediol); Picumeterol (4-amino-3,5-dichloro-α-(((6-(2-(2-pyridinyl)-ethoxy)hexyl)-amino)methyl)benzenemethanol); Pirbuterol (α⁶-(((1,1-dimethylethyl)amino)-methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-α¹-(((1,1-dimethylethyl)-amino)methyl)-4-hydroxy-1,3-benzenedimethanol); (R)-Salbutamol; Salmeterol ((±)-4-hydroxy-α¹-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)methyl)benzenem-ethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Of particular interest herein is formoterol, having the formula:

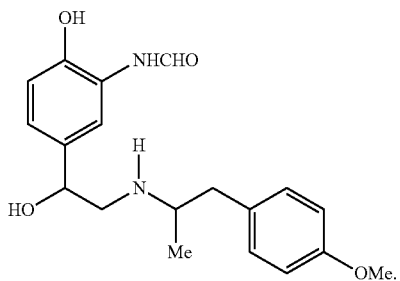

Formoterol for use in the compositions and methods provided herein includes 2-hydroxy-5-((1RS)-1-hydroxy-2-(((1RS)-2-(p-methoxyphenyl)-1-methylethyl)amino)ethyl)formanilide; or a stereoisomer thereof; and also includes the single enantiomers 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)amino)ethyl)formanilide.

In certain embodiments, the compositions are administered via nebulization. Administration of a nebulized aerosol is preferred over the use of dry powders for inhalation in certain subject populations, including pediatric and geriatric groups.

In one embodiment, the compositions for use in the methods provided herein contain a pharmaceutically acceptable derivative of formoterol. In another embodiment, the compositions for use in the methods provided herein contain a pharmaceutically acceptable salt of formoterol. Pharmaceutically acceptable salts include, but are not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. In one embodiment, the compositions for use in the methods provided herein contain formoterol fumarate or formoterol fumarate dihydrate. In another embodiment, the compositions for use in the methods provided herein contain formoterol tartrate.

Also provided herein are combinations containing a composition provided herein and a nebulizer. The combinations can be packaged as kits, which optionally contain other components, including instructions for use of the nebulizer. Any nebulizer is contemplated for use in the kits and methods provided herein. In particular, the nebulizers for use herein nebulize liquid formulations, including the compositions provided herein, containing no propellant. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large droplets from the mist by impaction and allows the droplets to return to the reservoir. The line aerosol droplets thus produced are entrained into the lung by the inhaling air/oxygen.

Methods for the treatment, prevention, or amelioration of one or more symptoms of bronchoconstrictive disorders, including, but not limited to, asthma, including, but not limited to, bronchial asthma, allergic asthma and intrinsic asthma, e.g., late asthma and airway hyper-responsiveness; chronic bronchitis; and other chronic obstructive pulmonary diseases are provided. The methods involve administering an effective amount of a pharmaceutical composition provided herein to a subject in need of such treatment.

Articles of manufacture, containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction, are also provided.

DETAILED DESCRIPTION

Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, formoterol refers to 2-hydroxy-5-((1RS)-1-hydroxy-2-(((1RS)-2-(p-methoxyphenyl)-1-methylethyl)amino)ethyl)formanilide; or a stereoisomer thereof. The term formoterol also refers to the single enantiomers 2-hydroxy-5-((1S)-1-hydroxy-2-(((1S)-2-(p-methoxyphenyl)-1-methylethyl)amino)ethyl)formanilide ((S,S)-formoterol) and 2-hydroxy-5-((1R)-1-hydroxy-2-(((1R)-2-(p-methoxyphenyl)-1-methylethyl)amino)-ethyl)formanilide ((R,R)-formoterol).

As used herein, formoterol fumarate refers to a salt of formoterol having the formula (formoterol).1/2 fumarate.

As used herein, formoterol free base refers to the neutral, anhydrous form of formoterol. Thus, a recitation that a composition contains, e.g., 20 µg/mL of formoterol free base means that the composition contains 20 µg/mL of neutral, anhydrous formoterol. Such compositions may be prepared using a derivative of formoterol.

As used herein, an aerosol is liquid or particulate matter dispersed in air. Aerosols include dispersions of liquids, including aqueous and other solutions, and solids, including powders, in air.

As used herein, a nebulized solution refers to a solution that is dispersed in air to form an aerosol. Thus, a nebulized solution is a particular form of an aerosol.

As used herein, a nebulizer is an instrument that is capable of generating very fine liquid droplets for inhalation into the lung. Within this instrument, the nebulizing liquid or solution is atomized into a mist of droplets with a broad size distribution by methods known to those of skill in the art, including, but not limited to, compressed air, ultrasonic waves, or a vibrating orifice. Nebulizers may further contain, e.g., a baffle which, along with the housing of the instrument, selectively removes large droplets from the mist by impaction. Thus, the mist inhaled into the lung contains fine aerosol droplets.

As used herein, a pharmacologically suitable fluid is a solvent suitable for pharmaceutical use which is not a liquified propellant gas. Exemplary pharmacologically suitable fluids include polar fluids, including protic fluids such as water.

As used herein, a kit refers to one or more items, including, but not limited to, compounds, compositions, combinations, instruments and devices, suitably packaged for use. Kits provided herein optionally contain instructions for use.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, a mixture is a mutual incorporation of two or more substances, without chemical union, the physical characteristics of each of the components being retained.

As used herein, the stability of a composition provided herein refers to the length of time at a given temperature that is greater than 80%, 85%, 90% or 95% of the initial amount of active ingredient, e.g., formoterol, is present in the composition. Thus, for example, a composition that is stable for 30 days at 25° C. would have greater than 80%, 85%, 90% or 95% of the initial amount of active ingredient present in the composition at 30 days following storage at 25° C.

As used herein, pharmaceutically acceptable derivatives of a compound include salts, esters, enol ethers, enol esters, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula $C=C(OR)$ where R is hydrogen, alkyl, alkenyl, alkynyl, aryl, heteroaryl, aralkyl, heteroaralkyl, cycloalkyl and heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, aralkyl, heteroaralkyl, cycloalkyl and heterocyclyl. Pharmaceutically acceptable solvates and hydrates are complexes of a compound with one or more solvent or water molecule, in certain embodiments 1 to about 100, in other embodiments 1 to about 10, in further embodiments one to about 2, 3 or 4, solvent or water molecules. Formoterol salts and hydrates are used in certain embodiments herein.

As used herein, treatment means any manner in which one or more of the symptoms of a condition, disorder or disease are ameliorated or otherwise beneficially altered. Treatment also encompasses any pharmaceutical use of the compositions herein, such as use for treating cancer.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds for use in the compositions and methods provided herein may contain chiral centers. Such chiral centers may be of either the (R) or (S) configuration, or may be a mixture thereof. Thus, the compounds for use in the compositions provided herein may be enantiomerically pure, or be stereoisomeric or diastereomeric mixtures. It is to be understood that the chiral centers of the compounds provided herein may undergo epimerization in vivo. Thus, one of skill in the art will recognize that administration of a compound in its (R) form is equivalent, for compounds that undergo epimerization in vivo, to administration of the compound in its (S) form.

As used herein, bronchoconstriction refers to a reduction in the caliber of a bronchus or bronchi.

As used herein, undesired and/or uncontrolled bronchoconstriction refers to bronchoconstriction that results in or from a pathological symptom or condition. Pathological conditions include, but are not limited to, asthma and chronic obstructive pulmonary disease (COPD). Pathological symptoms include, but are not limited to, asthma and COPD.

As used herein, the statement that a composition is stable during "long term storage" means that the composition is suitable for administration to a subject in need thereof when it has an estimated shelf-life of greater than 1, 2 or 3 months usage time at 25° C. and greater than or equal to 1, 2 or 3 years storage time at 5° C. In certain embodiments herein, using Arrhenius kinetics, >80% or >85% or >90% or >95% estimated bronchodilating agent remains after such storage.

A. Formoterol

Formoterol (2-hydroxy-5-((1RS)-1-hydroxy-2-(((1RS)-2-(p-methoxyphen-yl)-1-methylethyl)amino)ethyl)formanilide) is derived from adrenaline and, as noted above, is used as a $\beta_2$-stimulator in inhalation therapy of respiratory diseases, particularly for the treatment of bronchial asthma. It has been reported that in patients with reversible obstructive respiratory diseases, formoterol has a bronchodilatory effect. This effect has a relatively rapid onset (approximately 1-3 minutes) and a relatively long duration (greater than 12 hours). Formoterol inhibits the release of leukotrienes and other messenger substances involved with inflammation, such as histamines. In addition, formoterol may bring about a hyperglycemic activity.

To date, formoterol has been formulated as a dry powder and administered via devices such as the TURBUHALER® and the AEROLIZER®. See, e.g., Seberova et al. (2000) Respir. Med. 94(6):607-611; Lotvall et al. (1999) Can. Respir. J. 6(5):412-416; Campbell et al. (1.999) Respir. Med. 93(4):236-244; Nightingale et al. (1999) Am. J. Respir. Crit. Care Med. 159(6):1786-1790; Lecaillon et al. (1999) Eur. J. Clin. Pharmacol. 55(2):131-138; Bartow et al. (1998) Drugs 55(2):303-322; Ekstrom et al. (1998) Respir. Med. 92(8): 1040-1045; Ringdal et al. (1998) Respir. Med. 92(8):1017-1021; Totterman et al. (1998) Eur. Respir. J. 12(3):573-579; Palmqvist et al. (1997) Eur. Respir. J. 10(11):2484-2489; Nielsen et al. (1997) Eur. Respir. J. 10(9):2105-2109; Ullman et al. (1996) Allergy 51(10):745-748; Selroos et al. (1996) Clin. Immunother. 6:273-299; and Schreurs et al. (1996) Eur. Respir. J. 9(8): 1678-1683.

Formoterol is also available as a tablet and a dry syrup in certain areas of the world (e.g., ATOCK®, marketed by Yamanouchi Pharmaceutical Co. Ltd., Japan). Formoterol formulations are also available in other areas (e.g., Europe and U.S.) for propellant-based metered dose inhalers and dry powder inhalers (e.g., TURBUHALER®, AEROLIZER® AND FORADIL AEROLIZER®). None of these formulations are water based. Sterile, stable, aqueous based inhalation solutions of formoterol for nebulization are not available, nor have they been reported.

In the treatment of bronchoconstrictive diseases, sufficient amount of the inhaled drug should reach their local site of action in order to be efficacious. It is known that different delivery methods and delivery devices have different deposition characterstics. Consequently, under optimal inhalation conditions, doses from different delivery methods and delivery devices result in different delivered doses and different amounts deposited at the active site. The actual dose reaching the active site also depends upon the amount of drug particles included in the delivered dose and the inhalation characterstics of the patient. No correlation between the amount of drug administered by dry powder inhalers (DPIs) or metered dose inhalers (MDIs) and the actual amount that gets deposited at the active site has been established so far. Nor has a correlation been established between DPI or MDI dosages and nebulization dosages.

Compositions containing formoterol in combination with other active ingredients have been disclosed. See, e.g., U.S. Pat. Nos. 6,004,537, 5,972,919 and 5,674,860 (formoterol and budenoside), U.S. Pat. Nos. 5,668,110, 5,683,983, 5,677,280 and 5,654,276 (formoterol and IL-5 inhibitors), U.S. Pat. No. 6,136,603 (formoterol and antisense modulators of IL-5), U.S. Pat. No. 5,602,110 (formoterol and millrinone), U.S. Pat. No. 5,525,623 (formoterol and a tryptase inhibitor), U.S. Pat. Nos. 5,691,336, 5,877,191, 5,929,094, 5,750,549 and 5,780,467 (formoterol and a tachykinin receptor antagonist); and International Patent Application Publication Nos. WO 99/00134 (formoterol and rofleponide) and WO 99/36095 (formoterol and a dopamine $D_2$ receptor agonist).

Other compositions containing formoterol have been disclosed in U.S. Pat. Nos. 5,677,809, 6,126,919, 5,733,526, 6,071,971, 6,068,833, 5,795,564, 6,040,344, 6,041,777, 5,874,481, 5,965,622 and 6,161,536.

U.S. Pat. No. 6,150,418 discloses a "liquid active substance concentrate" containing formoterol in the form of its free base or in the form of one of the pharmacologically acceptable salts or addition products (adducts) thereof as active substance. This "liquid active substance concentrate" is reported to be a concentrated (i.e., greater than 10 mg/mL, preferably 75 to 500 mg/mL) solution or suspension that is stable for a period of several months possibly up to several years without any deterioration in the pharmaceutical quality. This patent teaches that it is the high concentration that allows for the stability of the concentrate. The "liquid active substance concentrate" is not suitable for direct administration to a patient.

U.S. Pat. No. 6,040,344 discloses an aqueous aerosol formulation of formoterol tartrate for use in a nebulizer. This patent states that the formulation disclosed therein is not attractive for long term storage.

B. Compositions for Use in Treatment, Prevention, or Amelioration of One or More Symptoms of Bronchoconstrictive Disorders Pharmaceutical compositions containing a $\beta_2$-adrenorecepto-r agonist for administration via nebulization are provided. The compositions are sterile filtered and filled in vials, including unit dose vials providing sterile unit dose formulations which are used in a nebulizer and suitably nebulized. Each unit dose vial is sterile and is suitably nebulized without contaminating other vials or the next dose.

The unit dose vials are formed in a form-fill-seal machine or by any other suitable method known to those of skill in the art. The vials may be made of plastic materials that are suitably used in these processes. For example, plastic materials for preparing the unit dose vials include, but are not limited to, low density polyethylene, high density polyethylene, polypropylene and polyesters. In one embodiment, the plastic material is low density polyethylene.

In one embodiment, the $\beta_2$-adrenoreceptor agonist is formoterol, or a pharmaceutically acceptable derivative thereof. In other embodiments, the formoterol for use in the compositions provided herein is formoterol fumarate. Formoterol refers to 2-hydroxy-5-((1RS)-1-hydroxy-1-2-(((1RS)-2-(p-methoxyphenyl)-1-methylethyl)amino)ethyl)formanilide; or a stereoisomer thereof. The term formoterol also refers herein to the single enantiomers. 2-hydroxy-5-((1S)-1-hydroxy-2-(((1S)-2-(p-methoxyphenyl)-1-methylethyl)amino)ethyl) formanilide and 2-hydroxy-5-((1R)-1-hydroxy-2-1-(((1R)-2-(p-methoxyphenyl)-1-methylethyl)amino)ethyl) formanilide.

In certain embodiments, the compositions contain formoterol fumarate at a concentration of about 0.1 µg/mL up to about 150 µg/mL, or 0.1 µg/mL up to 150 µg/mL. In further embodiments, the compositions contain formoterol fumarate at a concentration of about 0.1 µg/mL up to about 100 µg/mL, or 0.1 µg/mL up to 100 µg/mL. The formoterol fumarate is formulated, in certain compositions provided herein, at a concentration of about 0.1 µg/mL up to 50 µg/mL, or 0.1 g/mL up to 50 µg/mL. In further embodiments, the compositions contain formoterol fumarate at a concentration of about 0.1 µg/mL up to about 40 µg/mL, or 0.1 µg/mL up to 40 µg/mL. In further embodiments, the compositions contain formoterol fumarate at a concentration of about 0.1 µg/mL up to about 20 µg/mL, or 0.1 µg/mL up to 20 µg/mL. The formoterol fumarate is formulated, in other compositions provided herein, at a concentration of about 40 µg/mL, or 40 µg/mL. In further embodiments, the compositions contain formoterol fumarate at a concentration of about 35 µg/mL, or 35 λg/mL. In other embodiments, the compositions contain formoterol fumarate at a concentration of about 30 µg/mL, or 30 µg/mL. In other embodiments, the compositions contain formoterol fumarate at a concentration of about 25 µg/mL, or 25 g/mL. In further embodiments, the compositions contain formoterol fumarate at a concentration of about 20 µg/mL, or 20 µg/mL. In another embodiment, the compositions contain formoterol fumarate at a concentration of about 15 µg/mL, or 15 µg/mL. In another embodiment, the compositions contain formoterol fumarate at a concentration of about 12 µg/mL, or 12 µg/mL. In another embodiment, the compositions contain formoterol fumarate at a concentration of about 10 µg/mL, or 10 µg/mL. In another embodiment, the compositions contain formoterol fumarate at a concentration of about 8 µg/mL, or 8 µg/mL. In another embodiment, the compositions contain formoterol fumarate at a concentration of about 5 µg/mL, or 5 µg/mL. In another embodiment, the compositions contain formoterol fumarate at a concentration of about 2.5 µg/mL, or 2.5 µg/mL. In another embodiment, the compositions contain formoterol fumarate at a concentration of about 1 µg/mL, or 1 µg/mL.

In certain embodiments, the compositions contain formoterol free base at a concentration of about 0.08 µg/mL up to about 128 µg/mL, or 0.08 µg/mL up to 128 µg/mL. In further embodiments, the compositions contain formoterol free base at a concentration of about 0.08 µg/mL up to about 86 µg/mL, or 0.08 µg/mL up to 86 µg/mL. The formoterol free base is formulated, in certain compositions provided herein, at a concentration of about 0.08 µg/mL up to 43 µg/mL, or 0.08 µg/mL up to 43 µg/mL. In further embodiments, the compositions contain formoterol free base at a concentration of about 0.08 µg/mL up to about 34 µg/mL, or 0.08 µg/mL up to 34 µg/mL. In further embodiments, the compositions contain formoterol free base at a concentration of about 0.08 µg/mL up to about 26 µg/mL, or 0.08 µg/mL up to 26 µg/mL. The formoterol free base is formulated, in other compositions provided herein, at a concentration of about 0.08 µg/mL up to about 17 µg/mL, or 0.08 µg/mL up to 17 µg/mL. In further embodiments, the compositions contain formoterol free base at a concentration of about 34 µg/mL, or 34 µg/mL. In further embodiments, the compositions contain formoterol free base at a concentration of about 30 µg/mL, or 30 µg/mL. In other embodiments, the compositions contain formoterol free base at a concentration of about 25.6 µg/mL, or 25.6 µg/mL. In further embodiments, the compositions contain formoterol free base at a concentration of about 21.4 µg/L, or 21.4 µg/mL. In further embodiments, the compositions contain formoterol free base at a concentration of about 17 µg/mL, or 17 µg/mL. In another embodiment, the compositions contain formoterol free base at a concentration of about 13 µg/mL, or 13 µg/mL. In another embodiment, the compositions contain formoterol free base at a concentration of about. 10 µg/mL, or 10 µg/mL. In another embodiment, the compositions contain formoterol free base at a concentration of about 9 µg/mL, or 9 µg/mL. In another embodiment, the compositions contain formoterol free base at a concentration of about 7 µg/mL, or 7 µg/mL. In another embodiment, the compositions contain formoterol free base at a concentration of about 4 µg/mL, or 4 µg/mL. In another embodiment, the compositions contain formoterol free base at a concentration of about 2 µg/mL, or 2 µg/mL. In another embodiment, the compositions contain formoterol free base at a concentration of about 0.8 µg/mL, or 0.8 µg/mL.

The volume of formoterol inhalation solution nebulized depends on the nebulizer used. In certain embodiments, the volume is from about 0.1 mL up to about 3 mL, or 0.1 mL up to 3 mL. In other embodiments, the volume is about 2 mL, or 2 mL. In other embodiments, the volume is about 1 mL, or 1 mL. In other embodiments, the volume is about 0.5 mL, or 0.5 mL.

The compositions containing the $\beta_2$-adrenoreceptor agonist, including formoterol, are formulated with a pharmacologically suitable fluid. Pharmacologically suitable fluids include, but are not limited to, polar solvents, including, but not limited to, compounds that contain hydroxyl groups or other polar groups. Such solvents include, but are not limited to, water or alcohols, such as ethanol, isopropanol, and glycols including propylene glycol, polyethylene glycol, polypropylene glycol, glycol ether, glycerol and polyoxyethylene alcohols.

Polar solvents also include protic solvents, including, but not limited to, water, aqueous saline solutions with one or more pharmaceutically acceptable salt(s), alcohols, glycols or a mixture thereof. For a saline solution as the solvent or as a component thereof, particularly suitable salts are those which display no or only negligible pharmacological activity after administration.

In the embodiments herein, the compositions have a pH of about 2.0 to about 8.0, or 2.0 to 8.0. In other embodiments, the compositions have a pH of about 4.0 to about 6.0, or 4.0 to 6.0. In other embodiments, the pH is about 4.5 to about 5.5, or 4.5 to 5.5. In certain of the above embodiments, the compositions are formulated at a pH of about 4, 4.4 or 4.6 up to about 5.5, 5.7 or 6; or 4, 4.4 or 4.6 up to 5.5, 5.7 or 6. In other embodiments, the pH is about 5.0, or 5.0. It has been found that the rate constant for decomposition of an aqueous solution of formoterol is dependent on pH. The rate constant ($k_{obs}$) at 60° C. at a pH of 3, 4, 5 and 7 is approximately 0.62, 0.11, 0.044 and 0.55 day.sup.−1, respectively. Therefore, the decomposition of formoterol in aqueous solution at 60° C. at a buffer concentration of 5 mM and an ionic strength of 0.05 is slowest at a pH of about 5.0, or 5.0.

The solubility of formoterol in aqueous solution has been found to be dependent on pH. Thus, at a pH of between about 5 and about 7, the aqueous solubility of formoterol at ambient temperature is approximately 2.2 mg/mL. At a pH of about 4, the aqueous solubility of formoterol at ambient temperature is approximately 3 mg/mL, while at a pH of about 3, the aqueous solubility of formoterol at ambient temperature is about 4.8 mg/mL. The solubility of formoterol in pure water, for example, high performance liquid chromatography (HPLC) water, at ambient temperature is approximately 2 mg/mL.

In other of the above embodiments, the compositions further contain a buffer, including, but not limited to, citric acid/phosphate, acetate, barbital, borate, Britton-Robinson, cacodylate, citrate, collidine, formate, maleate, McIlvaine, phFosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxy-ethyl)imino-tris-(hydroxymethyl)methane), ADA (N-(2-acetamido)-2-iminodiacetic acid), ACES (N-(carbamoylmethyl)-2-aminoethanesulfonic acid), PIPES (piperazine-N,N'-bis(2-ethanesulfonic acid)), MOPSO (3-(N-morpholino)-2-hydroxypropanesulfonic acid), BISTRIS PROPANE (1,3-bis(tris(hydroxymethyl)methylamino)propane), BES (N,N-bis(2-hydroxyethyl)-2-aminoethanesulfonic acid), MOPS (3-(N-morpholino)propanesulfonic acid), TES (N-tris(hydroxymethyl)methyl-2-aminoethanesulfonic acid), HEPES (N-(2-hydroxyethyl)-piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris(hydroxymethyl)methylamino)-2-hydroxypropanesulfonic acid), TRIZMA® (tris(hydroxymethylaminomethane), HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxy-methyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxymethyl)methyl-3-aminopropanesulfonic acid), AMPD (2-amino-2-methyl-1,3-propanediol), and/or any other buffers known to those of skill in the art. In one embodiment, the buffer is citric acid/phosphate buffer, acetate buffer, citrate buffer or phosphate buffer. In another embodiment, the buffer is a citrate buffer (citric acid/sodium citrate). The buffer concentration has been found to affect the stability of the composition. Buffer concentrations for use include from about 0 or 0.01 mM to about 150 mM, or 0 or 0.01 mM to 150 mM. In another embodiment, the buffer concentration is about 1 mM to about 20 mM, or 1 mM to 20 mM. In one embodiment, the buffer concentration is about 5 mM, or 5 mM. In other embodiments, the buffer concentration is about 1 mM to about 50 mM, or 1 mM to 50 mM. In one embodiment, the buffer concentration is about 20 mM, or 20 mM. The kinetic-pH profile of formoterol is dependent on buffer concentration. At low and approximately neutral conditions, increasing the buffer concentration from 5 mM to 20 mM increased the rate constant of decomposition significantly. However, no noticeable differences in rate constant were observed in the pH region of about 4.5 to about 5.5, with increasing buffer concentration from 5 mM to 20 mM. The particular buffer and buffer concentration of a given composition for long term storage provided herein may be determined empirically using standard stability assays well known to those of skill in the art (see, e.g., the Examples).

The ionic strength of the compositions provided herein also has been found to affect the stability of the composition. Ionic strengths of the compositions provided herein are from about 0 to about 0.4, or 0 to 0.4. In another embodiment, the ionic strength of the compositions provided is about 0.05 to about 0.16, or 0.05 to 0.16. Compositions having a lower ionic strength exhibit improved stability over formulations having higher-ionic strength. The rate constant of decomposition was essentially the same at ionic strength 0.05 to 0.1, but increased to some extent at ionic strength of 0.2. The particular ionic strength of a given composition for long term storage provided herein may be determined empirically using standard stability assays well known to those of skill in the art (see, e.g., the Examples).

In embodiments where the pharmacologically suitable fluid is a saline solution, tonicity adjusting agents may be added to provide the desired ionic strength. Tonicity adjusting agents for use herein include those which display no or only negligible pharmacological activity after administration. Both inorganic and organic tonicity adjusting agents may be used in the compositions provided herein. Tonicity adjusting agents include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In certain embodiments, the tonicity adjusting agent is sodium chloride. In these embodiments, the pharmacologically suitable fluid is aqueous saline.

The storage temperature of the compositions provided herein also has been found to affect the stability of the composition. Compositions stored at a lower temperature exhibit improved stability over formulations stored at higher temperatures. The effect of temperature on the rate constant of decomposition at pH 5, a buffer concentration of 5 mM, and an ionic strength of 0.05, was linear according to Arrhenius kinetics, i.e., when $Ln\, k_{obs}$ was plotted against $1/T$, where T is the temperature in degree Kelvin.

The estimated shelf-life of formoterol in the compositions provided herein is significantly greater than that reported for known formoterol compositions. The estimated shelf-life of formoterol in the compositions provided herein is about 6.2 years, at 5° C. and about 7.5 months, or at 25° C. The estimated formoterol concentrations in the compositions provided herein as a function of storage time at 5° C. and usage time at 25° C. was determined. It is estimated that greater than 90% of the initial formoterol present in the composition remains after 3 months of usage time at 25° C. and 3 years of storage time at 5° C. as well as after 0.5 months of usage time at 25° C. and 1 year of storage time at 5° C.

In one embodiment, the compositions provided herein are prepared containing formoterol fumarate at a nominal concentration of 0.1 mg/mL at the indicated pH and citric acid/phosphate buffer concentrations. The solutions were stored at 60° C. In these compositions, formoterol is relatively more stable at a pH from about 4 to about 5, and is also more stable at lower buffer concentration.

The compositions provided herein also may include excipients and additives. The particular excipient or additive for use in the compositions for long term storage provided herein may be determined empirically using methods-well known to those of skill in the art (see, e.g., the Examples). Excipients and additives are any pharmacologically suitable and therapeutically useful substance which is not an active substance. Excipients and additives generally have no pharmacological activity, or at least no undesirable pharmacological activity. The excipients and additives include, but are not limited to, surfactants, stabilizers, complexing agents, antioxidants, or preservatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

The compositions provided herein also may include a cosolvent, which increases the solubility of additives or the active ingredient(s). The particular cosolvent for use in the compositions for long term storage provided herein may be determined empirically using methods well known to those of skill in the art. Cosolvents for use herein include, but are not limited to, hydroxylated solvents or other polar solvents, such as alcohols such as isopropyl alcohol, glycols such as propylene glycol, polyethylene glycol, polypropylene glycol, glycol ether, glycerol, and polyoxyethylene alcohols.

C. Preparation of Compounds for Use in the Compositions

The preparation of the compounds used in the compositions provided herein is described below. Any such compound or similar compound may be synthesized according to a method discussed in general below or by only minor modification of the methods by selecting appropriate starting materials.

Formoterol may be prepared according to the method disclosed in U.S. Pat. No. 3,994,974. Briefly, 4-benzyloxy-3-nitro-α-bromoacetophenone is reacted with N-benzyl-N-(1-methyl-2-p-methoxyphenylethyl)amine to form the α-aminoacetophenone. This compound was subjected to the following series of reactions: (i) reduction of the ketone with sodium borohydride; (ii) reduction of the nitro group with aqueous hydrochloric acid and iron powder; (iii) amine formylation with acetic anhydride and formic acid; and (iv) catalytic reduction over 10% palladium on carbon to afford formoterol free base. Crystallization of the ½ fumarate salt from ethanol provides (formoterol).½ fumarate.

The individual enantiomers of formoterol, 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)amino)ethyl)formanilide, may be prepared by the method disclosed in U.S. Pat. No. 6,040,344. Briefly, reaction of optically pure 4-benzyloxy-3-formamidostyrene oxide with an optically pure 4-methoxy-α-methyl-N-(phenylmethyl) benzene-ethanamine, followed by debenzylation, affords the desired enantiomer of formoterol. Debenzylation may be accomplished by reduction with hydrogen gas in the presence of a noble metal catalyst, such as palladium on carbon.

The required optically pure 4-benzyloxy-3-formamidostyrene oxide may be prepared from 4-benzyloxy-3-nitro-α-bromoacetophenone by (i) reduction with vorane in the presence of an optically pure aminoindanol, (ii) hydrogenation over platinum oxide catalyst, (iii) formylation with formic acid and acetic anhydride, and (iv) epoxide formation in the presence of potassium carbonate.

The required optically pure 4-methoxy-α-methyl-N-(phenylmethyl-1)benzeneethanamine may be prepared from 4-methoxyphenylacetone by (i) reductive amination with benzylamine in the presence of hydrogen and a platinum catalyst, and (ii) crystallization of the desired optically pure amine from the resulting racemic mixture as its mandelic acid salt.

D. Formulation of Pharmaceutical Compositions

The compositions provided herein are prepared by procedures well known to those of skill in the art. For example, a formoterol fumarate solution may be prepared by the procedure of Example 1. Briefly, a buffer solution having a pH and ionic strength of interest herein is prepared. In one embodiment, the buffer is a mixture of citric acid and sodium citrate, with sodium chloride added to achieve the desired ionic strength. Formoterol fumarate dihydrate is added to the buffer solution with agitation to produce a solution of the desired formoterol concentration. Exemplary formoterol concentrations is 0.0021 kg formoterol fumarate dihydrate/100 kg water.

E. Evaluation of the Activity of the Compositions

Standard physiological, pharmacological and biochemical procedures are available for testing the compositions provided herein to identify those that possess bronchodilatory activity.

In vitro and in vivo assays that may be used to evaluate bronchodilatory activity are well known to those of skill in the art. See also, e.g., U.S. Pat. Nos. 3,994,974, and 6,068,833; German Patent No. 2,305,092; Kaumann et al. (1985) Naunyn-Schmied Arch. Pharmacol. 331:27-39; Lemoine et al. (1985) Naunyn-Schmied Arch. Pharmacol. 331:40-51; Tomioka et al. (1981) Arch. Int. Pharmacodyn. 250:279-292; Dellamary et al. (2000) Pharm. Res. 17(2):168-174; Rico-Mendez et al. (1999) Rev. Alerg. Mex. 46(5):130-135; Seberova et al. (2000) Respir. Med. 94(6):607-611; Lotvall et al. (1999) Can. Respir. J. 6(5):412-416; Campbell et al. (1999) Respir. Med. 93(4):236-244; Nightingale et al. (1999) Am. J. Respir. Crit. Care Med. 159(6):1786-1790; Lecaillon et al. (1999) Eur. J. Clin. Pharmacol. 55(2):131-138; Bartow et al. (1998) Drugs 55(2):303-322; Ekstrom et al. (1998) Respir. Med. 92(8):1040-1045; Ringdal et al. (1998) Respir. Med. 92(8):1017-1021; Totterman et al. (1998) Eur. Respir. J. 12(3):573-579; Palmqvist et al. (1997) Eur. Respir. J. 10 (11):2484-2489; Nielsen et al. (1997) Eur. Respir. J. 10(9): 2105-2109; Ullman et al. (1996) Allergy 51(10):745-748; Selroos et al. (1996) Clin. Immunother. 6:273-299; and Schbreurs et al. (1996) Eur. Respir. J. 9(8):1678-1683.

F. Methods of Treatment of Bronchoconstrictive Disorders

The compositions provided herein are used for treating, preventing, or ameliorating one or more symptoms of a bronchoconstrictive disorders in a subject. In one embodiment, the method includes administering to a subject an effective amount of a composition containing a bronchodilating agent, including, but not limited to, formoterol, whereby the disease or disorder is treated or prevented. The subject treated is, in certain embodiments, a mammal. The mammal treated is, in certain embodiments, a human.

In another embodiment, the method provided herein includes oral administration of a composition provided herein. In certain embodiments herein, the composition is directly administered to a subject in need of such treatment via nebulization without dilution or other modification of the composition prior to administration.

The methods for treatment, prevention, or amelioration of one or more symptoms of bronchoconstrictive disorders, in another embodiment, further include administering one or more of (a), (b), (c) or (d) as follows: (a) a $β_2$-adrenoreceptor agonist; (b) a dopamine ($D_2$) receptor agonist; (c) a prophylactic therapeutic, such as a steroid; or (d) an anticholinergic agent; simultaneously with, prior to or subsequent to the composition provided herein.

$β_2$-Adrenoreceptor agonists for use in combination with the compositions provided herein include, but are not limited to, Albuterol ($α^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)

amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-dimethylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl-)amino) ethyl)-formanilide); (R,R)-Formoterol; Desformoterol ((R, R) or (S,S)-3-amino-4-hydroxy-α-(((2-(4-methoxyphenyl)-1-methylethyl)amino)methyl)benzenemethanol); Hexoprenaline (4,4'-(1,6-hexanediyl)-bis(imino(-1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)-amino) ethyl)-1,2-benzenediol-); Metaprotorenol (5-(1-hydroxy-2-((1-methylethyl)amino)ethyl)-1,3-benzene-diol); Picumeterol (4-amino-3,5-dichloro-α-(((6-(2-(2-pyridinyl) ethoxy)hexyl)-amino)methyl)benzenemethanol); Pirbuterol (α⁶-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(-1H)-quinolinone); Reproterol ((7-(3-((2-(3,5-dihydroxyphenyl)-2-hydroxyeth-yl)amino)-propyl)-3,7-dihydro-1,3-dimethyl-1H-purine-2,6-dione); Rimiterol (4-(hydroxy-2-piperidinylmethyl)-1,2-benzenediol); Salbutamol ((±)-α¹-(((1,1-dimethylethyl)-amino)-methyl)-4-hydroxy-1,3-benzenedimethanol); (R)-Salbutamol; Salmeterol ((±)-4-hydroxy-α¹-(((6-(4-phenylbutoxy)hexyl)amino)methyl)-1, 3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl) amino)-methyl)benzenemethanol); and TA-2005 (8-hydroxy-5-((1R)-1-hydroxy-2-(N-((1R)-2-(4-methoxyphenyl)-1-methylethyl)amino)ethyl)-carbostyril hydrochloride).

Dopamine (D₂) receptor agonists include, but are not limited to, Apomorphine ((r)-5,6,6a,7-tetrahydro-6-methyl-4H-dibenzo[de,g]quinoli-ne-10,11-diol); Bromocriptine ((5'α)-2-bromo-12'-hydroxy-2'-(1-methyl-lethyl)-5'-(2-methylpropyl)ergotaman-3',6',18-trione); Cabergoline ((8β)-N-(3-(dimethylamino)propyl)-N-((ethylamino)carbonyl)-6-(2-prop-enyl)ergoline-8-carboxamide); Lisuride (N'-((8α)-9, 10-didehydro-6-methylergolin-8-yl)-N,N-diethylurea); Pergolide ((8α)-8-((methylthio)methyl)-6-propylergoline); Levodopa (3-hydroxy-L-tryrosine); Pramipexole ((s)-4,5,6, 7-tetrahydro-N.sup.6-propyl-2,6-benzothiazolediamine); Quinpirole hydrochloride (trans-(−)-4aR-4,4a,5,6,7,8,8a,9-octahydro-5-pro-pyl-1H-pyrazolo[3,4-g]quinoline hydrochloride); Ropinirole (4-(2-(dipropylamino)ethyl)-1,3-dihydro-2H-indol-2-one); and Talipexole (5,6,7,8-tetrahydro-6-(2-propenyl)-4H-thiazolo[4,5-d]azepin-2-amine). Other dopamine D₂ receptor agonists for use herein are disclosed in International Patent Application Publication No. WO 99/36095.

Prophylactic therapeutics for use in combination therapy herein include steroidal anti-inflammatory agents, including, but not limited to, beclomethasone dipropionate (BDP), beclomethasone monopropionate (BMP), flunisolide, triamcinolone acetonide, dexamnethasone, tipredane, ciclesonid, rofleponide, mometasone, mometasone furoate (AS-MANEX® TWISTHALER™, Schering-Plough Corporation, Kentilworth, N.J.), RPR 106541, having the formula

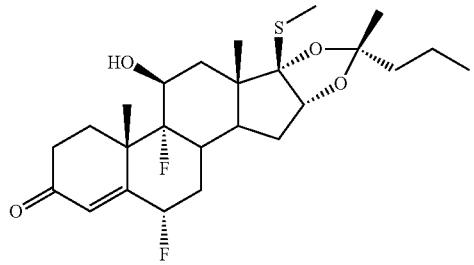

fluticasone or fluticasone propionate and budesonide or by way of sodium cromoglycate or nedocromil sodium.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, isopriopramide, orphenadrine, benzalkonium chloride, tiotropium bromide and glycopyrronium bromide. In certain embodiments, the compositions contain an anticholinergic agent, such as ipratropiumn bromide, at a concentration of about 100 μg/mL to about 500 g/mL, or 100 μg/mL to 500 μg/mL. In other embodiments, ipratropium bromide concentration is about 150 μg/mL to about 350 μg/mL, or 150 μg/mL to 350 μg/mL. In other embodiments, the compositions for use in the methods herein contain ipratropium bromide at a concentration of about 200 μg/mL to about 300 μg/mL, or 200 μg/mL to 300 μg/mL. In other embodiments, the compositions for use in the methods herein contain ipratropium bromide at a concentration of about 250 μg/mL, or 250 μg/mL.

Other active ingredients for use herein in combination therapy, include, but are not limited to, IL-5 inhibitors such as those disclosed in U.S. Pat. Nos. 5,668,110, 5,683,983, 5,677, 280 and 5,654,276; antisense modulators of IL-5 such as those disclosed in U.S. Pat. No. 6,136,603; milrinone (1,6-dihydro-2-methyl-6-oxo-[3,4'-bipyridine]-5-carb-onitrile milrinone lactate; tryptase inhibitors such as those disclosed in U.S. Pat. No. 5,525,623; tachykinin receptor antagonists such as those disclosed in U.S. Pat. Nos. 5,691,336, 5,877, 191, 5,929,094, 5,750,549 and 5,780,467; leukotriene receptor antagonists such as montelukast sodium (SINGULAR®, R-(E)]-1-[[[1-[3-[2-(7-chloro-2-quinolinyl)ethenyl-]phenyl]-3-[2-(1-hydroxy-1-methylethyl)-phenyl]-propyl]thio] methyl]cyclopro-paneacetic acid, monosodium salt), 5-lypoxygenase inhibitors such as zileuton (ZYFLO®, Abbott Laboratories, Abbott Park, Ill.), and anti-IgE antibodies such as XOLAIR® (recombinant humanized anti-IgE monoclonal antibody (CGP 51901; IGE 025A; rhuMAb-E25), Genentech, Inc., South San Francisco, Calif.).

The bronchoconstrictive disorder to be treated, prevented, or whose one or more symptoms are to be ameliorated is associated with asthma, including, but not limited to, bronchial asthma, allergic asthma and intrinsic asthma, e.g., late asthma and airway hyper-responsiveness; and, particularly in embodiments where an anticholinergic agent is used, other chronic obstructive pulmonary diseases (COPDs), including, but not limited to, chronic bronchitis, emphysema, and associated cor pulmonale (heart disease secondary to disease of the lungs and respiratory system) with pulmonary hypertension, right ventricular hypertrophy and right heart failure. COPD is frequently associated with cigarette smoking, infections, environmental pollution and occupational dust exposure.

G. Nebulizers

The compositions provided herein are intended for administration to a subject in need of such treatment via nebulization. Nebulizers that nebulize liquid formulations containing no propellant are suitable for use with the compositions provided herein. The nebulizer and can be unit dose or multidose. Nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwnvickshire, UK), Bard Ltd. (Sunderland, UK), Carri-Med Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many others.

Nebulizers for use herein include, but are not limited to, jet nebulizers (optionally sold with compressors), ultrasonic nebulizers, and others. Exemplary jet nebulizers for use herein include Pari LC plus/ProNeb, Pari LC plus/ProNeb Turbo, Pari LC plus/Dura Neb 1000 & 2000, Pari LC plus/Walkhaler, Pari LC plus/Pari Master, Pari LC star, Omron CompAir XL Portable Nebulizer System (NE-C18 and JetAir Disposable nebulizer), Omron CompAir Elite Compressor Nebulizer System (NE-C21 and Elite Air Reusable Nebulizer), Pari LC Plus or Pari LC Star nebulizer with Proneb Ultra compressor, Pulmo-aide; Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, SideStream Hand Held Neb, Mobil Mist, Up-Draft, Up-Draft II, T Up-Draft, ISO-NEB, AVA-NEB, Micro Mist, and PulmoMate. Exemplary ultrasonic nebulizers for use herein include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Nebulizer, Mystique Ultrasonic, Luminscope's Ultrasonic Nebulizer, Medisana Ultrasonic Nebulizer, Microstat Ultrasonic Nebulizer, and MABISMist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, AERONEB™ Portable Nebulizer System, AERODOSE™ Inhaler, AeroEclipse Breath Actuated Nebulizer, HALOLITE™ system (Profile Therapeutics), AKITA® systems (InaMed, Germany), Mystic system (BattellePharma), RESPIMAT® (Boehringer Ingelheim), AERX® (Aradigm), and E-FLOW™ (Pari).

Depending on the nebulizer used, the volume of the formoterol inhalation solution nebulized in one embodiment, is about 0.1 mL to 3 mL, or 0.1 mL to 3 mL. In another embodiment, the volume is about 2 mL, or 2 mL. In another embodiment, the volume is about 1 mL, or 1 mL. In another embodiment, the volume is about 0.5 mL, or 0.5 mL.

H. Articles of Manufacture

The compositions provided herein may be packaged as articles of manufacture containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

In one embodiment herein, the compositions are packaged with a nebulizer for direct administration of the composition to a subject in need thereof.

The following examples are included for illustrative purposes only and are not intended to limit the scope of the invention.

EXAMPLE 1

Preparation of Formoterol Inhalation Solution Formulation

Appropriate quantities of the raw materials are weighed for the 100 Kg batch as shown below:

| | 20 μg/mL* | 10 μg/mL* |
|---|---|---|
| Formoterol fumarate dihydrate | 0.0021 kg | 0.00105 kg |
| Citric acid monohydrate USP | 0.135 kg | 0.135 kg |
| Sodium Citrate dihydrate USP | 0.400 kg | 0.400 kg |
| Sodium chloride USP | 0.785 kg | 0.785 kg |
| Purified water USP | q.s. to 100 kg | q.s. to 100 kg |

*Concentration of formoterol fumarate (anhydrous)

In a clean stainless steel (SS) tank fitted with bottom drain, 75%.of the required amount of purified water is added. Samples are taken for pH, conductivity, and microbiological testing. Citric acid monohydrate, sodium citrate dihydrate and sodium chloride are added to the tank and mixed for 15 minutes to dissolve. A sample is taken at this point to check pH. Formoterol fumarate dihydrate is added at this point and mixed for about 75 minutes to dissolve all active raw material. Purified water is used to adjust to final volume. The formulation is mixed for an additional 30 minutes and samples for pH and assay are taken based on which the formulation is released for filling. The bulk solution is filled into low density polyethylene (LDPE) vials (2 mL fill) in a form-fill-seal (FFS) machine. The released drug product solution is transferred from the formulation tank through sanitary delivery lines into the FFS machine. The individual vials are overwrapped with a suitable foil laminate.

EXAMPLE 2

Procedure for Stability Testing of Formoterol Solutions

Stability samples of the solution prepared in EXAMPLE 1 and solution of formoterol fumarate (20 μg/mL) and ipratropium bromide (250 μg/mL) were placed in LDPE vials and stored in stability ovens at accelerated temperatures. At selected time points, aliquots of the samples were removed from the vials. The formoterol concentrations of the samples were analyzed by high performance liquid chromatography.

Provided herein is the stability data for exemplary formulations containing formoterol and formoterol in combination with ipratropium bromide.

Stability data on formoterol (20 μg/mL) and formoterol fumarate/ipratropium bromide combination (20 μg/ml and 250 μg/mL):

| Storage condition | Formterol Inhalation solution | Assay as percent of label claim Formoterol fumarate/ipratropium bromide inhalation solution | |
|---|---|---|---|
| | Formoterol | Formoterol | Ipratropium |
| Initial | 100 | 100.5 | 101.2 |
| 5° C./3 months | 96.7 | 100 | 101.6 |
| 25° C./3 months | 94.5 | 100 | 101.2 |

Since modifications will be apparent to those of skill in this art, it is intended that this invention be limited only by the scope of the appended claims.

What is claimed is:

1. A pharmaceutical composition, comprising formoterol, or a pharmaceutically acceptable derivative thereof selected from the group consisting of salts, esters, enol ethers, enol esters, acids, bases, solvates, hydrates and prodrugs, in a pharmacologically suitable fluid, wherein the composition is stable during long term storage and the fluid comprises water, and wherein the formoterol free base concentration is about 0.08 μg/mL up to about 128 μg/mL.

2. The pharmaceutical composition of claim 1, wherein the composition has an estimated shelf-life of greater than 1 month usage time at 25° C. and greater than or equal to 1 year storage time at 5° C.

3. The pharmaceutical composition of claim 1, wherein greater than about 80% of the initial formoterol is present after 1 month usage time at 25° C. and 1 year storage time at 5° C.

4. The pharmaceutical composition of claim 1 that has been nebulized.

5. The pharmaceutical composition of claim 1, wherein the pharmacologically suitable fluid comprises a polar solvent.

6. The pharmaceutical composition of claim 5, wherein the polar solvent is a protic solvent.

7. The pharmaceutical composition of claim 1, further comprising a tonicity adjusting agent.

8. The pharmaceutical composition of claim 7, wherein the tonicity adjusting agent is ammonium carbonate, ammonium chloride, ammonium lactate, ammonium nitrate, ammonium phosphate, ammonium sulfate, ascorbic acid, bismuth sodium tartrate,, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite,, sodium bromide, sodium cacodylate, sodium carbonate, sodium chloride, sodium citrate, sodium iodide, sodium lactate, sodium metabisulfite, sodium nitrate; sodium nitrite, sodium phosphate, sodium propionate, sodium succinate, sodium sulfate, sodium sulfite, sodium tartrate, sodium thiosulfate, sorbitol, sucrose, tartaric acid,, urea, urethan, uridine or zinc sulfate.

9. The pharmaceutical composition of claim 7, wherein the tonicity adjusting agent is sodium chloride.

10. The pharmaceutical composition of claim 1, wherein the pharmacologically suitable fluid comprises a buffer.

11. The pharmaceutical composition of claim 10, wherein the buffer is citric acid/phosphate, acetate, barbital, Britton-Robinson, cacodylate, citrate, collidine, formate, maleate, McIlvaine, phosphate, Prideaux-Ward, succinate,), verona acetate, MES (2-(N-morpholino)ethanesulfonic acid), ADA (N-(2-acetamido)-2-iminodiacetic acid), ACES (N-(carbamoylmethyl)-2-aminoethanesulfonic acid), PIPES (piperazine-N,N'-bis(2-ethanesulfonic acid)), MOPSO (3-(N-morpholino)-2-hydroxypropanesulfonic acid), BES (N,N-bis(2-hydroxyethyl)-2-aminoethanesulfonic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N-(2-ethanesulfonic 20 acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxymethyl)-methylamino)-2-hydroxypropanesulfonic acid), HEPPSO(N-(2-hydroxyethyl)piperazine-N'-(2-hydroxypropanesulfonic acid), POPSO (piperazine-N,N'-bis(2-hydroxypropanesulfonic acid)), EPPS(N-(2-hydroxyethyppiperazine-N'-(3-propanesulfonic acid), TRICINE (N-tris(hydroxymethyl) methylglycine), GLY-GLY (glycylglycine), BICINE (N,N-bis(2-hydroxyethyl)glycine), HEPBS (N-(2-hydroxyethyl) piperazine-N'-(4-butanesulfonic acid)), TAPS(N~tris(hydroxymethyl)methyl-3-aminopropanesulfonic acid), or AMPD (2-amino-2-methyl-1,3-propanediol) buffer.

12. The pharmaceutical composition of claim 10; wherein the buffer comprises citric acid/phosphate buffer, acetate buffer, citrate buffer or phosphate buffer.

13. The pharmaceutical composition of claim 10, wherein the buffer is citrate buffer.

14. The pharmaceutical composition of claim 13, wherein the buffer concentration is from about 0.01 mM to about 150 mM.

15. The pharmaceutical composition of claim 13, wherein the buffer concentration is from about 1 mM to about 50 mM.

16. The pharmaceutical composition of claim 13, wherein the buffer concentration is from about 1 mM to about 20 mM.

17. The pharmaceutical composition of claim 13, wherein the buffer concentration is about 20 mM.

18. The pharmaceutical composition of claim 13, wherein the buffer concentration is about 5 mM.

19. The pharmaceutical composition of claim 8, wherein the ionic strength of the composition is about 0 to about 0.4.

20. The pharmaceutical composition of claim 8, wherein the ionic strength of the composition is about 0.05 to about 0.16.

* * * * *